United States Patent [19]
Beard

[11] Patent Number: 4,622,966
[45] Date of Patent: Nov. 18, 1986

[54] SURGICAL CUTTING DEVICE

[75] Inventor: Robert W. Beard, Placerville, Calif.

[73] Assignee: Abbott Laboratories, North Chicago, Ill.

[21] Appl. No.: 631,536

[22] Filed: Jul. 16, 1984

Related U.S. Application Data

[60] Division of Ser. No. 278,955, Jun. 30, 1981, which is a continuation-in-part of Ser. No. 201,603, Oct. 28, 1980.

[51] Int. Cl.$^4$ ............................................. A61B 17/36
[52] U.S. Cl. .................. 128/303.14; 30/140; 219/233
[58] Field of Search ............... 128/305, 303.1, 303.14, 128/303.17; 219/233, 241, 499; 30/140

[56] References Cited

U.S. PATENT DOCUMENTS

| | | |
|---|---|---|
| 29,088 | 12/1976 | Shaw . |
| 30,190 | 1/1980 | Shaw . |
| 2,250,602 | 7/1941 | Pierce ..................................... 30/140 |
| 2,866,068 | 12/1958 | Bernstein et al. ...................... 30/140 |
| 2,960,592 | 11/1960 | Pierce ..................................... 30/140 |
| 3,208,142 | 9/1965 | Osrow ..................................... 30/140 |
| 3,352,011 | 11/1967 | Alexander et al. .................... 30/140 |
| 3,434,476 | 3/1969 | Shaw et al. . |
| 3,513,539 | 5/1970 | Davis ..................................... 219/233 |
| 3,685,518 | 8/1972 | Beverle et al. ................. 128/303.17 |
| 3,786,814 | 1/1974 | Armao ................................ 128/303.1 |
| 4,089,336 | 5/1978 | Cage et al. . |
| 4,091,813 | 5/1978 | Shaw et al. ............................ 30/140 |
| 4,119,836 | 10/1978 | Motokawa ............................ 30/140 |
| 4,139,760 | 2/1979 | Banks ..................................... 30/140 |
| 4,185,632 | 1/1980 | Shaw . |
| 4,198,957 | 4/1980 | Cage et al. ........................ 128/303.1 |
| 4,209,017 | 1/1980 | Shaw . |
| 4,231,371 | 11/1980 | Lipp .................................. 128/303.1 |
| 4,232,676 | 11/1980 | Herczog .......................... 128/303.17 |
| 4,314,559 | 2/1982 | Allen ..................................... 30/140 |
| 4,333,467 | 6/1982 | Danicone ....................... 128/303.14 |
| 4,412,123 | 10/1983 | Amman et al. ..................... 219/233 |

Primary Examiner—Edward M. Coven
Assistant Examiner—Max F. Hindenburg
Attorney, Agent, or Firm—Robert W. Stevenson; Martin L. Katz

[57] ABSTRACT

The cutting instrument of this invention is made by threading a heater assembly through a hollow cutting instrument body. A blade having a shank and a blade body including a cutting edge is secured within the hollow cutting instrument body at its shank portion such that the blade body extends from the hollow cutting instrument body. The heating assembly is secured to the blade body and to the cutting instrument body. The blade body is coated with a non-stick means.

7 Claims, 8 Drawing Figures

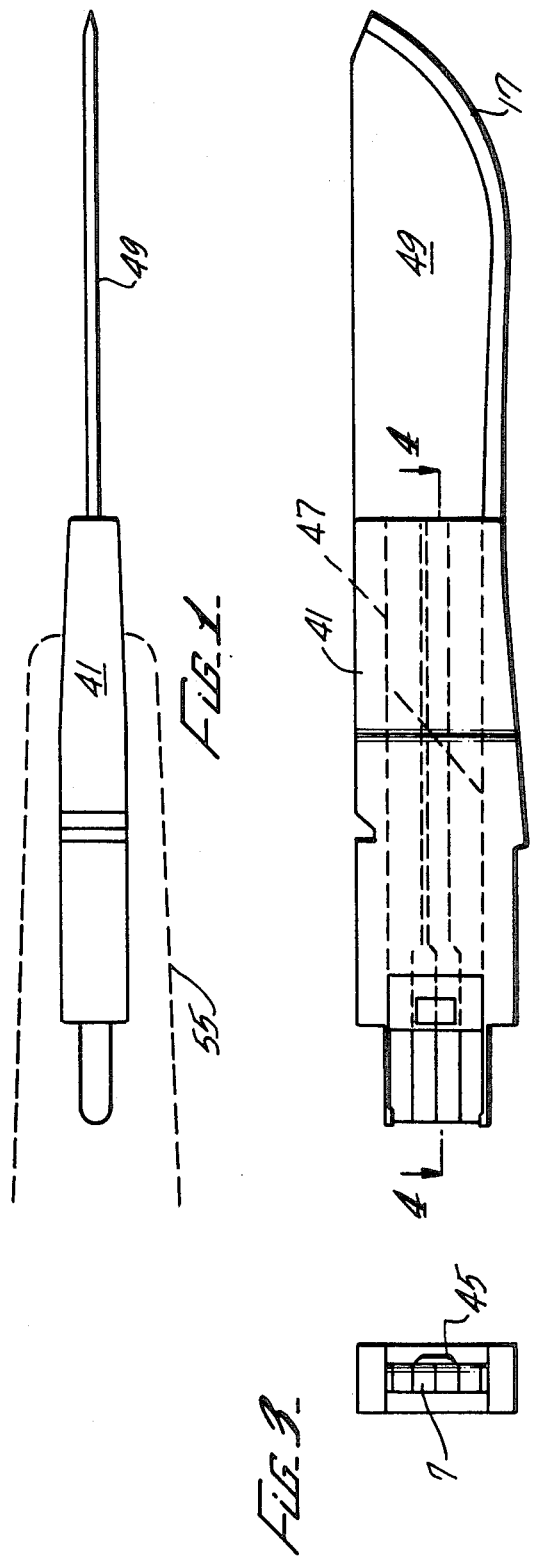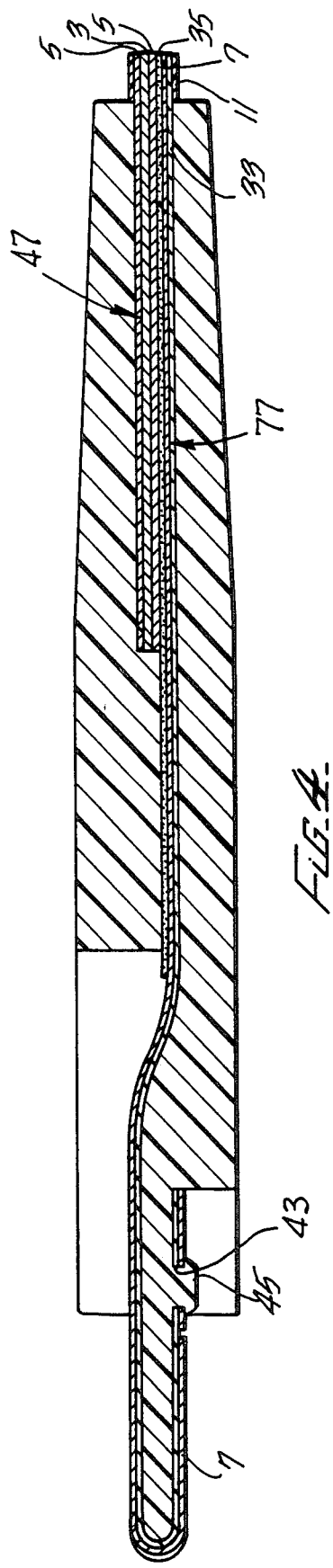

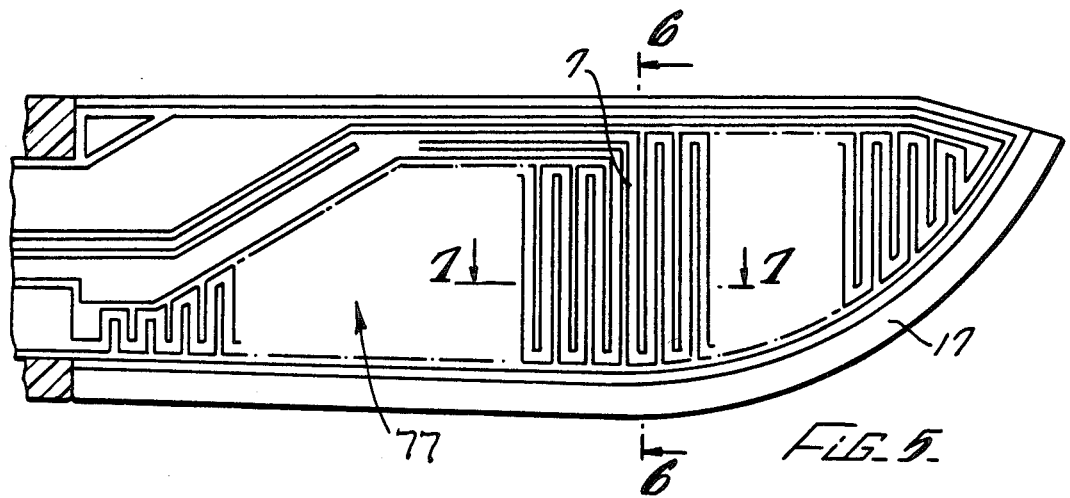
FIG. 5.
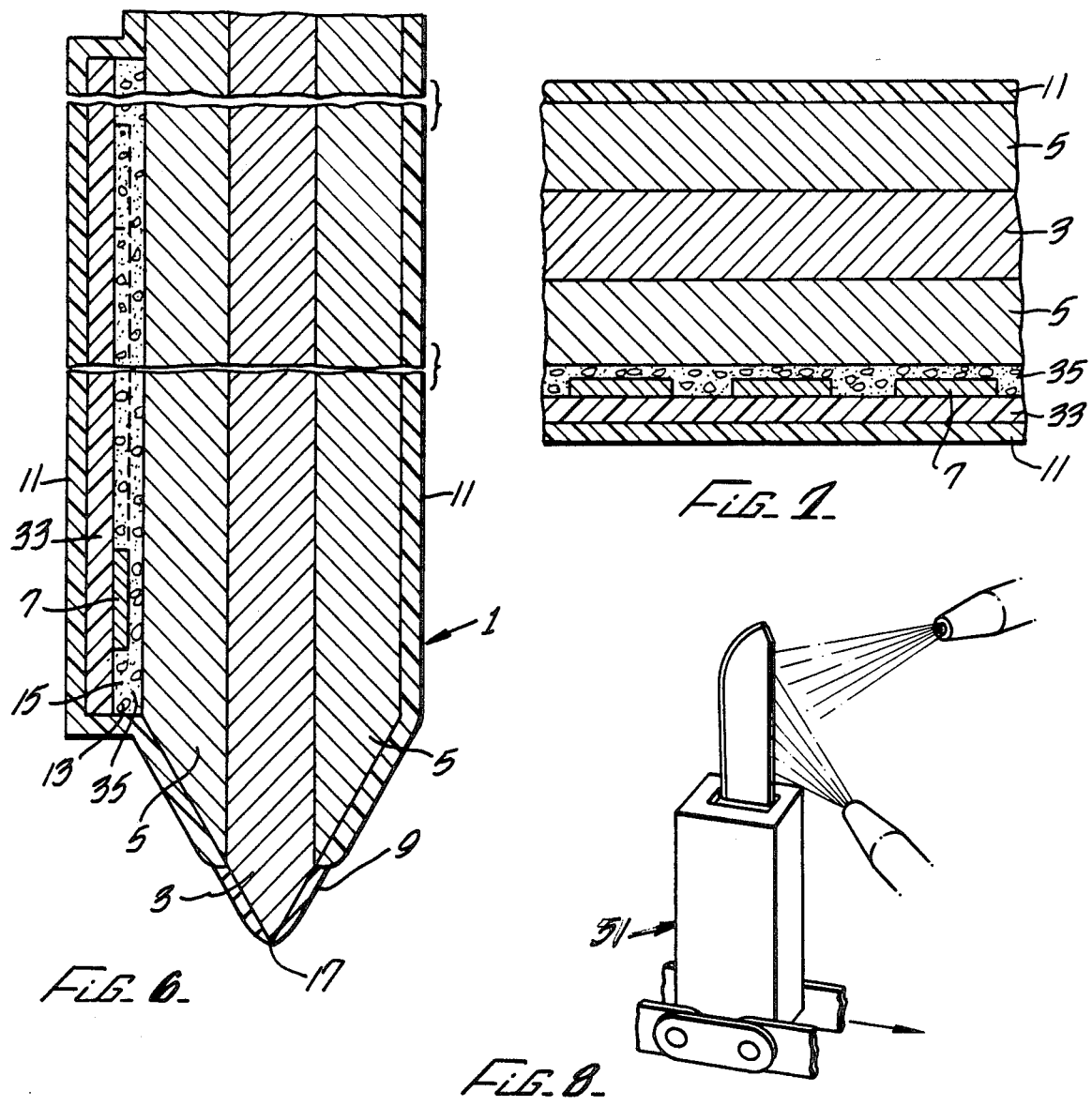
FIG. 6.
FIG. 7.
FIG. 8.

SURGICAL CUTTING DEVICE

CROSS-REFERENCE TO RELATED APPLICATIONS

This application is a division of application Ser. No. 278,955, filed June 30, 1981, which was a continuation-in-part of application Ser. No. 201,603, filed Oct. 28, 1980.

BACKGROUND OF THE INVENTION

The control of bleeding during surgery accounts for a major portion of the total time involved in a surgical operation. When tissue is incised, the attendant bleeding obscures the surgeon's vision, reduces his surgical precision and often dictates slow and elaborate procedures in surgical operation. Typically, each bleeding vessel must be grasped in a surgical clamp in order to stop the flow of blood and the tissue and vessel within each clamp is then tied with pieces of fine thread. Such ligated masses of tissue subsequently die and decompose thus tending to retard healing and providing a possible site for infection. A substantial amount of effort with regard to the heating of a cutting instrument so as to provide simultaneous hemostatis has been conducted by Robert F. Shaw and patents related to such efforts include U.S. Pat. No. Re. 29,088 which issued on Jan. 11, 1977, U.S. Pat. No. Re. 30,190 which issued on Jan. 15, 1980, U.S. Pat. No. 4,089,336 which issued on May 16, 1978, U.S. Pat. No. 4,091,813 which issued on May 30, 1978, and U.S. Pat. No. 4,185,632 which issued on Jan. 29, 1980.

DESCRIPTION OF THE DRAWINGS

FIGS. 1, 2 and 3 are pictorial views illustrating the subject matter of this invention;

FIG. 4 is a cross-sectional view taken about 4—4 of FIG. 2;

FIG. 5 is a partial pictorial view illustrating the subject matter of this invention;

FIGS. 6 and 7 are cross-section views taken about 3—3 and 4—4 of FIG. 5;

FIG. 8 is a pictorial view illustrating the subject matter of this invention.

DESCRIPTION OF THE PREFERRED EMBODIMENT

Referring now to FIG. 6 of the drawings, there is shown a cutting instrument 1 including a steel substrate 3. A copper composition 5 having a yield strength of at least 25,000 p.s.i. is laminated to the steel substrate 3. The copper composition 5 is preferably an alumina dispersion strengthened copper wherein the alumina present in the copper composition is from between about 0.1 and about 0.5 percent by weight of the total composition. Preferably the alumina-copper dispersion is of the type referred to and sold commercially as Glidcop by the Glidden Company. The steel substrate 3 and copper composition laminate 5 should be capable of experiencing a heat treatment at least to a temperature of approximately 1500 degrees F.

A heater asembly 77, including a heater means 7 preferably formed of copper in a strip is secured to the copper composition laminate 5 by means of an adhesive 35 that includes an electrically insulative and thermally conductive filler material 13 admixed with a material 15 selected from the group consisting of acrylic, polyimide, polyamide, silicone, phenolic, and epoxy resins. The adhesive filler material 13 is preferably made up of industrial grade diamonds. In one embodiment, the diameter of such industrial grade diamond filler material 13 is such that the material spans the distance between the heater means 7 and the copper composition 5.

The steel substrate 3 includes a cutting edge 17 which is preferably coated with a non-stick means 9 in order to preclude the cutting edge from sticking to a subject upon which a cutting operation is performed. Further, at least a portion of the balance of the cutting instrument is also similarly coated by non-stick means 11. Preferably the non-stick means 9 applied to the cutting edge 17 is a dispersion of fluorocarbon particles within a silicone adhesive binder while the non-stick means applied to the balance of the cutting instrument is a fluorocarbon composition. The non-stick means 9 and 11 are preferably a form of polytetrafluoroethylene and chosen from the group consisting of tetrafluoroethane, polyfluorinated alcoxy and fluorinated ethylene polymer. In a preferred embodiment the heater assembly includes a polyimide backing material 33 upon which the heater means 7 and adhesive 35 may be disposed prior to being secured to the copper composition 5. The cutting blade assemblies are stacked one atop the other such that each blade body is masked by the next adjacent blade body and the cutting edges 17 sprayed with a non-stick 9. The cutting instrument 1 is manufactured by threading the heater assembly 77 including the heater means 7 and its attendant backing material 33 and adhesive 35 through the hollow cutting instrument body 41 as shown in FIG. 4. The distal end of this heater assembly 77 preferably includes an aperture 43 which is secured about peg 45 of the hollow cutting instrument body. The shank 47 of the steel blade 3 is secured within the hollowing cutting instrument body 41 such that the blade body 49 and cutting edge 17 extend from the hollow cutting instrument body 41. The proximal portion of heating assembly 77 is then laminated to the blade body 49 as shown in FIG. 6. This laminating process is preferably carried out at a pressure between about 100 p.s.i. and about 500 p.s.i. and a temperature between about 100° C. and about 250° C. Preferably the hollow cutting blade body 41 is of a thermoplastic material such that peg 45 may be heated so as to expand and heat stake the distal end of the heater assembly 77 to the hollow cutting blade body 41.

Then the assemblies are placed in a boot conveyor 51 with the blade body 49 extending outward and the blade body 49 is coated with a non-stick 11.

The heater assembly 77 preferably includes a heater means 7 of copper such that that portion of the heater means 77 which wraps about the distal end of the hollow cutting instrument body 41 and attaches at peg 45 allows for electrical contact with the portion of heater assembly 77 in contact with the laminate of steel 3 and copper composition 5. Thus the heater assembly 77 directly interfaces between the blade laminate of steel 3 and copper composition 5 and the hollow cutting instrument body 41 adapted to be directly inserted in surgical handle 55 and make electrical contact therewith without intermediate conductors.

The structure of the present invention having been described, its method of operation will now be discussed. Upon application of electrical current from an external power heater means 7 is heated and heat is thermally conducted through the adhesive 35 to the copper composition 5 and the steel substrate 3 with its cutting edge 17. Such heat transfer from the heater means 7 to the steel substrate 3 is carried out in accordance with the heat transfer equation $q=K\,a(\text{delta }T/\text{delta }X)$ where q is the amount of heat transferred, K is the thermal heat transfer coefficient, a is the area through which the heat is transferred, delta T is the differential temperature and delta x is the thickness of the material through which the heat is transferred.

In a preferred embodiment, the thickness of the steel substrate 3 is approximately 6 mils and the thickness of the copper composition 5 is approximately 6 mils. Further, the thickness of the heater means 7 is preferably approximately 0.4 mils, while the thickness of the adhesive 35 is preferably about 0.4 mils. The backing material 33 is preferably approximately 2 mils in thickness. Due to the physical parameters regarding heat transfer, the cutting instrument of the present invention allows for the cutting instrument 1 to be maintained at a substantially constant temperature within a predetermined range of preferably between about 100 degrees C. and about 300 degrees C.

It is obvious that certain changes can be made to the preferred form of the invention as described above. Accordingly, the claims should be given an interpretation commensurate with the scope of the invention as set out in the claims appended hereto.

What is claimed is:

1. A surgical instrument capable of being heated to a predetermined temperature within a predetermined temperature range, comprising:

a blade body having a steel substrate with a cutting edge and a copper composition having a yield strength of at least 25,000 p.s.i. laminated to said steel substrate, but not extending so as to cover the cutting edge of said steel substrate;

a hollow cutting instrument body which engages the blade body;

heater means passing through said hollow cutting instrument body and directly interfacing and secured at its proximal end to said blade body and at its distal end to said cutting instrument body; and non-stick means coated on said cutting edge and at least a portion of the balance of said blade body.

2. The instrument claimed in claim 1 wherein said copper composition is an alumina dispersion strengthened copper, said alumina being present in said laminate from between about 0.1 and about 0.5 percent by weight.

3. The instrument claimed in claim 1 wherein said heater means is secured to said copper composition by means of an adhesive which includes an electrically insulative and thermally conductive filler material admixed with a material selected from the group consisting of acrylic and epoxy resins.

4. The instrument claimed in claim 3 wherein said filler material contains a plurality of industrial grade diamonds.

5. The instrument claimed in claim 4 wherein the diameter of at least some of said diamonds is substantially the same as the distance between said laminate and said heater.

6. The instrument claimed in claim 1 wherein said non-stick means applied to said cutting edge is a dispersion of fluorocarbon particles within a silicon adhesive binder and the non-stick means applied to the balance of said cutting instrument is a fluorocarbon composition.

7. The instrument claimed in claim 6 wherein the fluorocarbon of said non-stick means is teflon.

* * * * *